(12) United States Patent
Hoffmann et al.

(10) Patent No.: US 6,417,190 B1
(45) Date of Patent: Jul. 9, 2002

(54) TRICYCLIC NITROGEN HETEROCYCLES AS PDE IV INHIBITORS

(75) Inventors: Matthias Hoffmann, Ingelheim am Rhein; Birgit Jung, Schwabenheim; Ulrike Kuefner-Muehl, Ingelheim am Rhein; Christopher John Montague Meade, Bingen am Rhein, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/458,789

(22) Filed: Dec. 10, 1999

Related U.S. Application Data
(60) Provisional application No. 60/127,777, filed on Apr. 5, 1999.

(30) Foreign Application Priority Data
Dec. 17, 1998 (DE) .......................................... 198 58 331

(51) Int. Cl.$^7$ ............................................. A61K 31/505
(52) U.S. Cl. ....................................... 514/267; 514/912
(58) Field of Search ................................. 514/267, 912

(56) References Cited
U.S. PATENT DOCUMENTS
5,744,473 A    4/1998  Chasin et al.
6,136,810 A  * 10/2000  Takayama et al. .......... 514/258

FOREIGN PATENT DOCUMENTS
WO    WO 99 65912    12/1999
WO    WO 00 12511     3/2000

OTHER PUBLICATIONS
Tenor, E. Et Al; "Synthese und Reaktivitaet von 7–Amino–s–triazolo{1.5–alpha]pyrimidonen–(5)", Chemische Berichte, Verlag Chemie GMBH, vol. 97, No. 97, 1964, p. 1373–1383.

\* cited by examiner

*Primary Examiner*—Zohreh Fay
(74) *Attorney, Agent, or Firm*—Robert P. Raymond; Philip I. Datlow; Alan R. Stempel

(57) ABSTRACT

The invention relates to the use of tricyclic nitrogen heterocycles of general formula I

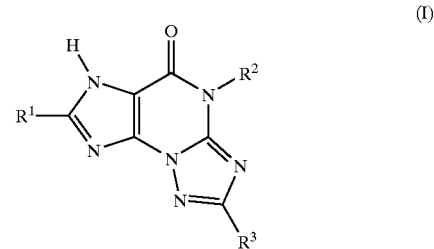

as pharmaceutical compositions with an inhibitory effect on PDE IV, wherein the groups $R^1$, $R^2$ and $R^3$ have the meanings given in the specification and claims.

9 Claims, No Drawings

TRICYCLIC NITROGEN HETEROCYCLES AS PDE IV INHIBITORS

This application claims benefit under 35 U.S.C. §119(e) to Provisional Application No. 60/127,777, filed Apr. 5, 1999.

The invention relates to the use of tricyclic nitrogen heterocycles of general formula I

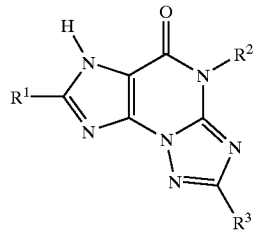

as pharmaceutical compositions with an inhibiting effect on PDE IV, wherein the groups $R^1$, $R^2$ and $R^3$ may have the meanings given in the following part of the description and in the claims.

BACKGROUND OF THE INVENTION

Cyclic nucleotide-phosphodiesterases (PDEs) bring about degradation of the second messenger cAMP and cGMP to 5'-AMP and 5'-GMP. The second messenger cAMP and cGMP trigger the activation of protein kinases and hence the phosphorylation of proteins. By hydrolysing cAMP and cGMP to form the inactive nucleotides 5'-AMP and 5'-GMP, PDEs prevent the activation of the protein kinases. Phosphodiesterases are divided up into different classes of PDE isoenzymes, depending inter alia on their different substrate specificities, different kinetic properties, etc. The family of the PDE I isoenzymes is activated by means of the intracellular receptor protein for $Ca^{2+}$ ions kalmodulin ($Ca^{2+}$/kalmodulin-stimulated PDE). PDE II isoenzymes are cGMP-stimulated phosphodiesterases with little affinity for cAMP and cGMP. The family of the PDE III isoenzymes (cGMP-inhibited) is characterised by a high affinity for cAMP and cGMP. Type IV phosphodiesterases (PDE IV) mean cAMP-specific PDEs which have a high affinity for cAMP but a low affinity for cGMP. PDE V isoenzymes are cGMP-specific while having a low affinity for CAMP.

PDE inhibitors influence the concentration of intracellular cAMP and cGMP. Of particular interest is the selective inhibition of type IV phosphodiesterase which leads to an increase in the concentration of intracellular cAMP.

Type IV phosphodiesterase (PDE) inhibitors are known from the prior art. One of the most prominent examples of the compounds which selectively inhibit the PDE IV isoenzyme is rolipram which has the following chemical structure.

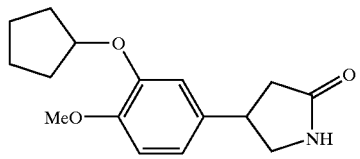

PDE IV inhibitors cause vasodilatation (reduction in the tone of the smooth muscle), have a partial positive inotropic effect and also have anti-inflammatory properties.

Accordingly, PDE IV inhibitors may have a therapeutic effect in the treatment and prophylaxis of diseases in which the above effects caused by increasing the cAMP concentration are expected and desirable.

DETAILED DESCRIPTION OF THE INVENTION

Surprisingly, it has been found-that tricyclic heterocycles of general formula (I) wherein the groups $R^1$, $R^2$ and $R^3$ are as hereinafter defined are selective inhibitors of type IV phosphodiesterase.

The invention consequently relates to the use of tricyclic nitrogen heterocycles of general formula I

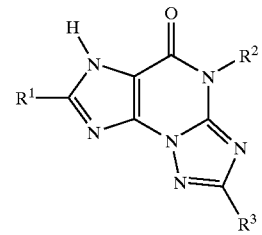

as pharmaceutical compositions with a PDE IV inhibiting activity, wherein $R^1$ denotes $C_1$–$C_5$-alkyl, $C_5$–$C_6$-cycloalkyl, phenyl, benzyl or a 5- or 6-membered, saturated or unsaturated heterocyclic ring which may contain one or two heteroatoms, selected from the group comprising oxygen and nitrogen;

$R^2$ denotes $C_1$–$C_5$-alkyl or $C_2$–$C_4$-alkenyl;

$R^3$ denotes $C_1$–$C_5$-alkyl, which may optionally be substituted by $C_1$–$C_4$-alkoxy, $C_5$–$C_6$-cycloalkyl, phenoxy or by a 5- or 6-membered, saturated or unsaturated heterocyclic ring which may contain one or two heteroatoms, selected from the group comprising oxygen and nitrogen, $C_5$–$C_6$-cycloalkyl or phenyl or benzyl optionally substituted by $C_1$–$C_4$-alkoxy, optionally in the form of their racemates, enantiomers; in the form of their diastereomers and mixtures thereof, optionally in the form of their tautomers and optionally the pharmacologically acceptable addition salts thereof.

It is preferable to use the compounds of general formula (I) as described above, wherein $R^1$ may denote $C_{1-4}$-alkyl, $C_{5-6}$-cycloalkyl, tetrahydrofuranyl, tetrahydropyranyl, piperazinyl, morpholinyl or phenyl;

R2 may denote $C_{1-4}$-alkyl or $C_{2-4}$ alkenyl;

R3 may denote $C_{1-4}$-alkyl which may optionally be substituted by $C_{1-4}$-alkoxy, $C_{5-6}$-cycloalkyl, phenoxy, ($C_{1-4}$-alkoxy)phenyloxy, piperazine or pyrrole, or R3 may denote $C_{5-6}$-cycloalkyl, or phenyl or benzyl optionally substituted by $C_{1-4}$-alkoxy, optionally in the form of their racemates, their enantiomers, in the form of their diastereomers and mixtures thereof, optionally in the form of their tautomers and optionally the pharmacologically acceptable acid addition salts thereof.

It is also preferable to use compounds of general formula (I) as described above, wherein $R^1$ denotes ethyl, propyl, butyl, cyclopentyl, tetrahydrofuranyl, tetrahydropyranyl, N-morpholinyl or phenyl;

$R^2$ denotes ethyl, propyl, allyl or butenyl;
$R^3$ denotes ethyl, propyl, butyl, cyclopentyl, cyclohexylmethyl, benzyl, phenylethyl, phenoxymethyl, methoxybenzyl or N-pyrrolylmethyl,
optionally in the form of their racemates, enantiomers, in the form of their diastereomers and mixtures thereof, optionally in the form of their tautomers and optionally the pharmacologically acceptable addition salts thereof.

It is particularly preferred to use compounds of general formula (I) as described above, wherein $R^1$ denotes ethyl, n-propyl, tert-butyl, cyclopentyl, 3-tetrahydrofuryl, N-morpholinyl or phenyl;
$R^2$ denotes ethyl or n-propyl;
$R^3$ denotes ethyl, i-propyl, n-propyl, n-butyl, t-butyl, cyclopentyl, cyclohexylmethyl, benzyl, phenylethyl, phenoxymethyl, 4-methoxybenzyl or N-pyrollylmethyl, optionally in the form of their racemates, enantiomers, in the form of their diastereomers and mixtures thereof, optionally in the form of their tautomers and optionally the pharmacologically acceptable addition salts thereof.

If desired, the compounds of general formula (I) may be converted into the salts thereof, particularly for pharmaceutical use into the physiologically acceptable salts thereof with an inorganic or organic acid. Suitable acids for this purpose include, for example, succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the abovementioned acids.

Suitable alkyl groups (including those which are part of other groups) are branched and unbranched alkyl groups with 1 to 5 carbon atoms, such as: methyl, ethyl, n-propyl, iso-propyl, n-butyl, iso-butyl, sec. butyl, tert.-butyl, n-pentyl, iso-pentyl or neo-pentyl. The abbreviations Me, Et, n-Pr, i-Pr, n-Bu, i-Bu, t-Bu, etc. may be used for the abovementioned groups.

Examples of cycloalkyl groups with 5 or 6 carbon atoms include cyclopentyl or cyclohexyl. Examples of 5- or 6-membered, saturated or unsaturated heterocyclic rings which may contain one or two heteroatoms selected from the group comprising oxygen and nitrogen, include: furan, tetrahydrofuran, tetrahydrofuranone, γ-butyrolactone, α-pyran, γ-pyran, dioxolane, tetrahydropyran, dioxane, pyrrole, pyrroline, pyrrolidine, pyrazole, pyrazoline, imidazole, imidazoline, imidazolidine, pyridine, piperidine, pyridazine, pyrimidine, pyrazine, piperazine, morpholine, oxazole, isoxazole, oxazine, pyrazolidine.

The compounds of general formula (I) may be prepared analogously to the method described in the prior art for some examples of the compounds of general formula (I) described hereinbefore (Tenor et al., Chem. Ber. Vol. 97 (1964) S. 1373–1382), the contents of which are hereby referred to.

The present invention is directed not only to the application mentioned at the beginning but also to the use of the above compounds of general formula (I) for preparing pharmaceutical compositions for the treatment or prevention of diseases in which the selective inhibition of the PDE IV enzyme is indicated.

The present invention also relates to the use of compounds of general formula (I) for the treatment or prevention of diseases in which a therapeutically desirable effect can be achieved by increasing the concentration of intracellular cAMP. Accordingly, the present invention is directed to the use of compounds of general formula (I) according to the above definitions for increasing the concentration of intracellular cAMP. The use of the compounds of general formula (I) according to the above definitions for preparing a pharmaceutical composition for increasing the concentration of intracellular cAMP is a further aspect of the present invention.

PDE IV inhibitors have a bronchodilatory or even an anti-inflammatory effect in the lungs. The compounds of general formula (I) according to the above definitions can therefore be used to treat asthma or C.O.P.D. (chronic obstructive pulmonary disease).

PDE IV inhibitors inhibit the influx of eosinophiles after an allergic stimulus. The compounds of general formula (I) according to the above definitions can consequently be used to treat allergic illnesses such as e.g. allergic rhinitis, allergic conjunctivitis and allergic eye diseases.

Since PDE IV inhibitors also inhibit the release of cytokines such as TNF-alpha by macrophages, the above-defined compounds of general formula (I) can be expected to be effective in the treatment of diseases such as e.g. Adult Respiratory Distress Syndrome or inflammatory arthritis, where the release of TNF is involved.

The above-defined compounds of general formula (I) may also be therapeutically useful for the treatment and prevention of the diseases listed below: asthma, particularly asthma in inflammation of the lungs, inflammation of the lungs and airways, C.O.P.D. (chronic obstructive pulmonary disease), cystic fibrosis, chronic bronchitis, eosinophilic granuloma, inflammatory skin diseases such as psoriasis, ischaemia, endotoxic or septic shock, ulcerative colitis, Crohn's disease, rheumatoid arthritis, chronic glomerulonephritis, urticaria, conjunctivitis vernalis, multiple sclerosis or arteriosclerosis.

Table 1 contains the pharmacological data obtained for the compounds of general formula (I). The data was obtained by the method of Torphy et al. (1992), J. Pharmacol. Exp. Ther. 263:1195.

TABLE 1

(I)

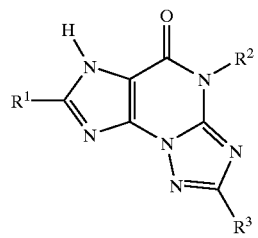

| No. | $R^1$ | $R^2$ | $R^3$ | $IC_{50}$ [μM] * (human PDE IV) |
|---|---|---|---|---|
| 1 | Cyclopentyl | n-propyl | i-propyl | 0.018 |
| 2 | Cyclopentyl | n-propyl | ethyl | 0.039 |
| 3 | t-butyl | ethyl | 4-methoxybenzyl | 0.042 |
| 4 | cyclopentyl | ethyl | —CH$_2$CH$_2$phenyl | 0.046 |
| 5 | 3-tetrahydro-furyl | ethyl | benzyl | 0.048 |
| 6 | cyclopentyl | n-propyl | n-propyl | 0.049 |
| 7 | t-butyl | ethyl | benzyl | 0.053 |
| 8 | phenyl | n-propyl | n-propyl | 0.055 |
| 9 | cyclopentyl | ethyl | benzyl | 0.057 |
| 10 | -n-propyl | -n-propyl | benzyl | 0.069 |
| 11 | cyclopentyl | ethyl | N-pyrrolylmethyl | 0.069 |
| 12 | cyclopentyl | -n-propyl | benzyl | 0.074 |
| 13 | cyclopentyl | -n-propyl | -t-butyl | 0.079 |
| 14 | cyclopentyl | n-propyl | n-butyl | 0.081 |
| 15 | cyclopentyl | ethyl | —CH$_2$-Ophenyl | 0.11 |
| 16 | N-morpholinyl | -n-propyl | benzyl | 0.11 |
| 17 | cyclopentyl | ethyl | cyclohexylmethyl | 0.11 |

TABLE 1-continued (I)

[Chemical structure of formula (I) showing a fused heterocyclic system with substituents R¹, R², R³ and NH, C=O groups]

| No. | R¹ | R² | R³ | IC$_{50}$ [μM] * (human PDE IV) |
|-----|-----|-----|-----|-----|
| 18 | ethyl | ethyl | cyclohexylmethyl | 0.12 |
| 19 | n-propyl | n-propyl | cyclopentyl | 0.12 |

*Experimental conditions - enzyme: purified from human monocytes (U937-cells);
Final volume of the assays: 0.1 ml;
protein: between 2 μg/measuring point and 6 μg/measuring point (depending on the degree of purification of the enzyme);
incubation buffer: 40 mM Tris-HCl (pH 7.8), 3 mM MgCl2;
radioligand: 1 μCi/ml [3H] cAMP;
incubation: 30 min at 30° C.;
Reference inhibitor: Rolipram The compounds of general formula (I) may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dosage is between 1 and 800 mg, preferably between 10 and 300 mg per adult.

The Examples which follow illustrate the present invention without restricting its scope:

EXAMPLES OF PHARMACEUTICAL FORMULATIONS

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Coated tablets | per coated tablet |
|---|---|
| active substance | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are mixed thoroughly and moistened with water. The moist mass is forced through a sieve with a mesh size of 1 mm, dried at about 45° C. and the granules are passed through the same sieve again. After the addition of magnesium stearate, convex tablet cores with a diameter of 6 mm are pressed out in a tablet-making machine. The tablet cores thus produced are coated in known manner with a coating which consists mainly of sugar and talc. The finished coated tablets are polished with wax.

| D) Capsules | per capsule |
|---|---|
| active substance | 50 mg |
| corn starch | 268.5 mg |
| magnesium stearate | 1.5 mg |
| | 320 mg |

The active substance and corn starch are mixed together and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| active substance | 50 mg |
| solid fat | 1650 mg |
| | 1700 mg |

The hard fat is melted. At 40° C. the ground active substance is homogeneously dispersed. It is cooled to 38° C. and poured into slightly chilled suppository moulds.

| G) Oral Suspension | |
|---|---|
| active substance | 50 mg |
| hydroxyethylcellulose | 50 mg |
| sorbic acid | 5 mg |
| sorbitol (70%) | 600 mg |
| glycerol | 200 mg |
| flavour | 15 mg |
| water | ad 5 ml |

Distilled water is heated to 70° C. Hydroxyethylcellulose is dissolved therein with stirring. After the addition of sorbitol solution and glycerol the mixture is cooled to ambient temperature. At ambient temperature, sorbic acid, flavouring and active substance are added. The suspension is evacuated with stirring in order to eliminate air.

What is claimed is:

1. A method of treating a disease in a warm-blooded animal, said disease being treatable by inhibiting the production of type IV phosphodiesterase in said animal, which comprises administering to said animal a type IV phosphodiesterase production-inhibiting amount of a tricyclic, nitrogen heterocycle of formula I

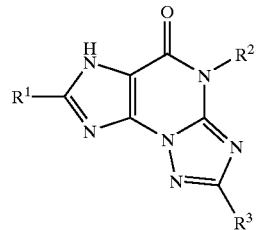

wherein
   $R^1$ is $C_1$–$C_5$-alkyl, $C_5$–$C_6$-cycloalkyl, phenyl, benzyl or a 5- or 6-membered, saturated or unsaturated heterocyclic ring which may contain one or two heteroatoms, selected from the group consisting of oxygen and nitrogen;
   $R_2$ is $C_1$–$C_5$-alkyl or $C_2$–$C_4$-alkenyl;
   $R_3$ is $C_1$–$C_5$-alkyl, which may optionally be substituted by $C_1$–$C_4$-alkoxy, $C_5$–$C_6$-cycloalkyl, phenoxy or by a 5- or 6-membered, saturated or unsaturated heterocyclic ring which may contain one or two heteroatoms, selected from the group consisting of oxygen and nitrogen, $C_5$–$C_6$-cycloalkyl or phenyl or benzyl optionally substituted by $C_1$–$C_4$-alkoxy, in the form of racemate, an enantiomer, a diastereomer or a mixture thereof, or in the form of a tautomer or a pharmacologically acceptable addition salt thereof.

2. The method as recited in claim 1 wherein in the tricyclic, nitrogen heterocycle
   $R_1$ is $C_1$–$C_4$-alkyl, $C_5$–$C_6$-cycloalkyl, tetrahydrofuranyl, tetrahydropyranyl, piperazinyl, morpholinyl or phenyl;
   $R_2$ is $C_{1-4}$-alkyl or $C_{2-4}$-alkenyl;
   $R_3$ is $C_{1-4}$-alkyl, which may optionally be substituted by $C_1$–$C_4$-alkoxy, $C_{5-6}$-cycloalkyl, phenoxy, ($C_{1-4}$-alkoxy) phenyloxy, piperazine or pyrrole, $C_{5-6}$-cycloalkyl or phenyl or benzyl optionally substituted by $C_{1-4}$-alkoxy.

3. The method as recited in claim 2 wherein in the tricyclic, nitrogen heterocycle
   $R_1$ is ethyl, propyl, butyl, cyclopentyl, tetrahydrofuranyl, tetrahydropyranyl, N-morpholinyl or phenyl;
   $R_2$ is ethyl, propyl, allyl or butenyl; and
   $R_3$ is ethyl, propyl, butyl, cyclopentyl, cyclohexylmethyl, benzyl, phenylethyl, phenoxymethyl, methoxybenzyl or N-pyrrolylmethyl.

4. The method as recited in claim 3 wherein in the tricyclic, nitrogen heterocycle
   $R^1$ is ethyl, n-propyl, tert-butyl, cyclopentyl, 3-tetrahydrofuryl, N-morpholinyl or phenyl;
   $R^2$ is ethyl or n-propyl; and
   $R^3$ is ethyl, i-propyl, n-propyl, n-butyl, t-butyl, cyclopentyl, cyclohexylmethyl, benzyl, phenylethyl, phenoxymethyl, 4-methoxybenzyl or N-pyrollylmethyl.

5. A method of claim 1, wherein said administration results in an increase in the concentration of intracellular cAMP in said animal.

6. A method of claim 1, wherein said administration results in an inhibition of the production of TNF in said animal.

7. A method of claim 1, wherein said disease is selected from the group consisting of asthma, C.O.P.D., allergic rhinitis, allergic conjunctivitis, allergic eye diseases, adult respiratory distress syndrome, inflammatory arthritis, inflammation of the lungs and airways, cystic fibrosis, chronic bronchitis, eosinophilic granuloma, psoriasis, ischaemia, endotoxic shock, septic shock, ulcerative colitis, Crohn's disease, rheumatoid arthritis, chronic glomerulonephritis, urticaria, conjunctivitis vernalis, multiple sclerosis and arteriosclerosis.

8. The method as recited in claim 7 wherein the disease is asthma.

9. The method as recited in claim 7 wherein the disease is C.O.P.D.

* * * * *